United States Patent [19]

DeMasi et al.

[11] 4,453,979

[45] Jun. 12, 1984

[54] DISPERSION OF HYDROPHILIC GUMS TO FORM NON-SWELLING AQUEOUS ALCOHOLIC MIXTURES

[75] Inventors: Dominick F. DeMasi, Norwood, N.J.; Gregg S. Scheideler, Hauppauge, N.Y.

[73] Assignee: Lever Brothers Company, New York, N.Y.

[21] Appl. No.: 477,810

[22] Filed: Mar. 23, 1983

[51] Int. Cl.$^3$ .................... C08L 1/08; A01N 25/00; A61K 7/16

[52] U.S. Cl. .................... 106/188; 106/189; 106/208; 424/49; 424/73; 424/78; 424/362

[58] Field of Search ............... 106/188, 189, 208, 213, 106/311; 424/49, 73, 78, 362

[56] References Cited

U.S. PATENT DOCUMENTS

| | | | |
|---|---|---|---|
| 2,662,882 | 12/1953 | Christianson et al. | 536/2 |
| 2,807,591 | 9/1957 | Henry | 252/363.5 |
| 2,970,063 | 1/1961 | Jordan et al. | 180/19 R |
| 3,446,764 | 5/1969 | Phillips et al. | 106/188 |
| 3,485,651 | 12/1969 | Ganz | 106/208 |
| 3,503,895 | 3/1970 | Whelan | 106/208 |
| 3,899,439 | 8/1975 | Mahlman | 106/189 |
| 4,221,601 | 9/1980 | Augustin | 106/189 |
| 4,263,050 | 4/1981 | Yamanaka et al. | 106/311 |
| 4,309,535 | 1/1982 | Majewicz | 536/85 |

FOREIGN PATENT DOCUMENTS

| | | | |
|---|---|---|---|
| 48-52848 | 7/1973 | Japan . | |
| 2000799 | 1/1979 | United Kingdom | 106/188 |

OTHER PUBLICATIONS

Industrial Gums, Whistler; Roy L., Mar. 14, 1974.

*Primary Examiner*—Theodore Morris
*Attorney, Agent, or Firm*—Milton L. Honig; James J. Farrell

[57] ABSTRACT

A process is presented for dispersing hydrophilic gums swiftly into formulations containing water wherein the lumping problem is avoided.

The method of obtaining lump-free aqueous gum compositions comprises:

(a) preparing a blend of water and an effective amount of water-miscible alcohol (I):

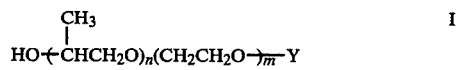

wherein n and m are the same or different integers from 0 to 500, and when Y is hydrogen, (I) has a molecular weight of at least 200, and when Y is $C_1$–$C_4$ alkyl, (I) has a molecular weight of at least 32;

(b) introducing into said aqueous alcohol blend a hydrophilic gum, resulting in a final weight ratio water:gum of about 20:1 to 1.3:1;

(c) intimately mixing the resultant slurry; and (d) feeding the slurry into a water containing formulation.

9 Claims, No Drawings

DISPERSION OF HYDROPHILIC GUMS TO FORM NON-SWELLING AQUEOUS ALCOHOLIC MIXTURES

BACKGROUND OF THE INVENTION

1. Field of the Invention

This invention relates to a method for avoiding lump formation when hydrophilic gums are dispersed in aqueous systems and to compositions resulting therefrom.

2. The Prior Art

Hydrophilic gums are widely used in industry. They are formulated into pharmaceuticals, cosmetics, personal care products, papers and other diverse compositions. Their functions include acting as thickeners, binders, stabilizers, protective colloids, suspending agents and rheology or flow control agents. Generally, gums are blended directly into aqueous solutions. Upon contact with water, these materials swell and convert to viscous gel-like sols.

Rapid addition of hydrophilic gum to water is highly desirable. Unfortunately, rapid contact with water frequently results in lumping. More controlled addition only partially circumvents the problem. The lumps are gel-like substances, wet on the outside, dry in the center. Lumps usually resist dispersion even upon vigorous agitation or cooking. Once formed, extraordinary efforts are needed to effect their removal. Not only time, but considerable material is lost during removal.

Commercially, lumping has been avoided by pre-swelling the dry gums prior to addition into aqueous systems. Slow, careful wetting of gum with minor amounts water accomplishes the pre-swelling. Yet lumping is seldom totally avoided. The wetting process is time consuming. Production rates of end-product must be slowed to the rate limiting step, i.e., the pre-swell process.

Numerous patents record attempts to solve the problem by designing more readily dispersible gums. For instance, U.S. Pat. No. 2,662,882 modifies the gum by pre-wetting with water, agglomerating, regrinding and drying at room temperature. Dry-mixing gum with sodium bicarbonate or carbonate and an acid such as sodium bisulfite yields readily dispersible powders according to U.S. Pat. No. 2,807,591. In U.S. Pat. No. 4,309,535, sodium carboxymethyl cellulose, hereinafter referred to as CMC, was treated with aluminum chloride dissolved in aqueous isopropanol; drying afforded easily dispersible particles. British Pat. No. 926,409 disclosed that treatment of CMC with a fine water spray in a pulsating trough yielded a power of 5% moisture content with improved dispersibility. Other easily dispersible powders have been reported obtainable where CMC has undergone treatment either with aqueous sodium sulfate, been sprayed with aqueous Sorbit, or been stirred with aqueous mono- and di-glycerides, see Japanese Patent Nos. 78:45,358, 78:65,489 and 80:61,928, respectively. In Japanese Patent No. 73:52,848 cellulose derivatives were swelled with approximately an equivalent weight of water containing a small amount polyethylene glycol. After drying, gum granules were obtained that upon dissolution in water afforded lump-free solutions.

All the aforementioned art has pertained to modifying gum powders to enhance their water solubility. In contrast, the literature is relatively silent concerning direct methods to improve processing of hydrophilic gums into aqueous consumer products. Even with modified powders, blending difficulties are often noted. New techniques are still needed to increase gum-water blending efficiency that avoids lumping.

It is an object of this invention to present a process for dispersing hydrophilic gums swiftly into water containing formulations while avoiding the lumping problem.

It is a further object to provide lump-free compositions comprising hydrophilic gums, water and alcohol.

SUMMARY OF THE INVENTION

A method of formulating a lump-free aqueous gum containing composition is disclosed comprising:

(a) preparing a blend of water and an effective amount of water-miscible alcohol (I):

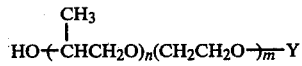

wherein n and m are the same or different integers from 0 to 500, and when Y is hydrogen, (I) has a molecular weight of at least 200, and when Y is $C_1$-$C_4$ alkyl, (I) has a molecular weight of at least 32;

(b) introducing into said aqueous alcohol blend a hydrophilic gum, resulting in a final weight ratio water:gum of about 20:1 to 1.3:1;

(c) intimately mixing the resultant slurry; and (d) feeding the slurry into a water containing formulation.

DETAILED DESCRIPTION OF THE INVENTION

Although lumping can be prevented by slow addition, where gums are dispersed into aqueous systems, lumps called fisheyes still form. This is undesirable. We have discovered that when a dry gum is first wetted with moist water-soluble alcohol, the resultant composition can be rapidly added to aqueous solutions without causing fisheye problems. Unexpectedly, swelling does not occur even in the presence of relatively high moisture levels in the alcohol solution.

"Slurries" of gum-alcohol-water are easily handleable. The convenience of fluid, pumpable slurries at ambient temperature is of economic significance in plant scale operations. Considerable time is saved. Production rates are increased. Material waste is diminished. Especially significant is that normally solid alcohols can be made fluid at ambient temperatures with water; then safely combined with hydrophilic gums.

The invention is applicable to a variety of gums. Typical gums include the mannan type such as guar, locust bean, honey locust, flametree, paloverde, tara, cassia occidentalis; as well as the pathological exudate type of gums such as tragacanth, karaya, arabic and so forth. Other useful gums of natural origin include xanthan, pectin, alginates, carrageenan, furcellaran and agar. Particularly preferred gums are xanthan, carrageenan and quaternized guar gum. "Polymer JR" and "Jaguar C" are trademarks representing a preferred quaternary nitrogen-containing cellulose ether and a quaternized guar gum sold by Union Carbide and Celanese Corporations, respectively.

Synthetic and natural polymeric carbohydrates and derivatives may be used with this process. Examples of such materials include starch, modified starch, sodium carboxyalkyl cellulose (CMC), hydroxyalkyl alkylcellulose, hydroxyalkyl cellulose, alkyl cellulose and mixtures thereof wherein alkyl is $C_1-C_4$. Particularly preferred modified cellulosics are methyl cellulose, hydroxypropyl methylcellulose and sodium carboxymethyl cellulose.

The alcohols to be used with this invention are not merely solvents. In fact, their function as solvent for gum is ancillary. They perform a dual function. All the alcohols employed herein are necessary components of the final consumer formulation. Alcohols impart humectancy, clarity, viscosity control and other properties to the consumer end-product.

Among the useful alcohols are the polymeric glycols such as polyethylene glycol, polypropylene glycol, polyoxyethylene-polyoxypropylene block copolymers and mixtures thereof. Their molecular weights must be at least 200. Lesser molecular weight glycols such as ethylene glycol, diethylene glycol and triethylene glycol when combined with water are ineffective to prevent lumping. Polyethylene and polypropylene glycols can range in molecular weight from about 200 to about 25,000. Preferred molecular weight ranges are from about 200 to 4000. Polyalkylene glycols are obtainable from the Union Carbide Corporation under the trademark "PEG;" for instance, PEG-32 being a polyethylene glycol of molecular weight 1500. The Dow Chemical Corporation also sells these materials under its "Polyglycol E" series of trademarks; for instance Polyglycol E-200, E-300 and E-1540 have molecular weights identical to their respective numbers. Mixed polyoxypropylene-polyoxyethylene glycol systems can be obtained from the BASF-Wyandotte Corporation sold under the trademark "Pluronic".

Monohydric alcohols can also be employed in this process. Lower alkanols such as methanol, ethanol, isopropanol, n-propanol, t-butanol, s-butanol and mixtures thereof are all suitable. Water-miscible monohydric ethylene glycol derivatives are also effective in this process. Examples include 2-methoxy ethanol (methyl cellosolve), 2-(2-methoxy ethoxy)-ethanol, 2-ethoxy ethanol (ethyl cellosolve), 2-butoxy ethanol (butyl cellosolve) and mixtures thereof.

The process involved in this invention is a simple one. A clean reactor is charged with alcohol and water; the order of addition is unimportant. Where a reactor still contains remnants of gum-water-alcohol from a previous charge, alcohol must first be added for the new charge. While the aqueous alcohol solution is being mixed, gum is added to the reactor. Once gum has been fully dispersed in the aqueous alcohol solution, the resultant slurry is ready for addition to the main water containing formulation. Heat may be applied but is generally not necessary in the pre-wetting step. Dependent upon the precise components in the main water containing formulation, heat thereunto may be necessary during addition of the pre-wetted gum slurry.

The amount of alcohol to hydrophilic gum can range from about 25:1 to about 2:1. Preferably, the ratio of alcohol to gum should range from about 12:1 to about 3:1. The amounts of water to gum ranges from about 20:1 to about 1.3:1. Preferably, the water to gum ratio should be about 6:1 to about 2:1.

The optimum ratio of alcohol to gum to water may vary depending on each particular alcohol and gum. One approach for determining optimum ratios is here suggested. First an alcohol to gum ratio of 3:1 is prepared and mixed well. The composition is then titrated with water until swelling occurs. At the swelling point is the maximum allowable water concentration.

The following examples will more fully illustrate the embodiments of this invention. All parts, percentages and proportions referred to herein and in the appended claims are by weight unless otherwise illustrated.

EXAMPLE I

A series of different alcohols wetted with water were evaluated for their non-lumping properties with various gums. Water and alcohol were placed into 2-ounce wide-mouth jars. Gum was added last. The combinations were stirred manually using a microspatula and subsequently shaken vigorously within the sealed jar. Table 1 lists the results. Both the alcohol and distilled water concentrations were held constant—at 5 and 2 parts, respectively. Gum concentrations were varied.

Under the results column, the plus symbol (+) indicates pourable fluid after standing at room temperature for 4 hours; this is a desirable result. Those entries with a negative symbol (−) signify that the mixture gelled and/or localized clumping was seen due to gum swelling.

Low molecular weight glycols such as ethylene glycol, diethylene glycol and triethylene glycol afforded lumps. CMC when mixed with wet glycerol formed a gel. These alcohols were unsuitable with the instant invention.

TABLE 1

| Alcohol[a] | Gum (parts) | | Results |
|---|---|---|---|
| Polyethylene Glycol - 1500 | CMC | (.4) | + |
| " | CMC | (.7) | + |
| " | CMC | (1.0) | + |
| " | CMC | (1.5) | + |
| Polyethylene Glycol - 1500 | Methocel E4M[e] | (.4) | + |
| " | Methocel E4M | (.7) | + |
| " | Methocel E4M | (1.0) | + |
| Polyethylene Glycol - 1500 | Xanthan | (.4) | + |
| " | Carrageenan | (.4) | − |
| " | Jaguar C-17[f] | (.4) | + |
| " | Methocel A-100[g] | (.4) | + |
| Polyethylene Glycol - 200 | CMC | (.4) | + |
| " | CMC | (.7) | + |
| " | CMC | (1.0) | + |
| " | CMC | (1.5) | + |
| Polyethylene Glycol - 200 | Methocel E4M | (.4) | + |
| " | Methocel E4M | (.7) | + |
| " | Methocel E4M | (1.0) | + |
| Polyethylene Glycol - 300 | CMC | (.4) | + |
| " | CMC | (1.0) | + |
| Ethylene Glycol | CMC | (.4) | − |
| Diethylene Glycol | CMC | (.4) | − |
| Triethylene Glycol | CMC | (.4) | − |
| Ethyl Cellosolve | CMC | (.4) | + |
| Polyethylene Glycol - 4000 | CMC | (.4) | + |
| " | CMC | (.7) | + |
| " | Methocel E4M | (.4) | + |
| Polyethylene Glycol - 400 | CMC | (.4) | Borderline |
| Polyethylene Glycol - 400 | CMC | (1.0) | Borderline |
| Dipropylene Glycol | CMC | (.4) | + |
| Dipropylene Glycol | Methocel E4M | (.4) | − |
| 3A Alcohol[b] | CMC | (.4) | + |
| " | CMC | (1.0) | + |
| " | CMC | (1.5) | + |
| 3A Alcohol | Methocel E4M | (.4) | − |
| 3A Alcohol | Xanthan | (.4) | + |
| " | Carrageenan | (.4) | + |
| " | Jaguar C-17 | (.4) | + |
| Isopropanol | CMC | (.4) | + |
| 2-Methoxyethanol | CMC | (.4) | + |
| 2-(2-Methoxyethoxy)-ethanol | CMC | (.4) | + |
| tert-Butyl Alcohol | CMC | (.4) | + |
| Glycerol | CMC | (.4) | − |
| Sorbitol (70% solids)[c] | CMC | (.4) | − |

TABLE 1-continued

| Alcohol[a] | Gum (parts) | | Results |
|---|---|---|---|
| Butyl Cellosolve | CMC | (.4) | + |
| " | CMC | (1.0) | − |
| Butyl Cellosolve | Methocel E4M | (.4) | − |
| Butyl Cellosolve | Xanthan | (.4) | Borderline |
| Butyl Cellosolve | Carrageenan | (.4) | + |
| " | Jaguar C-17 | (.4) | + |
| " | Methocel A-100 | (.4) | + |
| Pluronic L62D[d] | CMC | (.4) | + |
| " | CMC | (1.0) | + |
| Pluronic L62D | Methocel E4M | (.4) | + |
| Pluronic L62D | Methocel A-100 | (.4) | + |

Footnotes:
[a] Alcohol and water are present at 5 and 2 parts, respectively. Numbers hyphenated to the polyglycols represent molecular weight.
[b] Mixture of primarily ethanol and small amounts of methanol.
[c] Sold by the Roquette Freres Company and ICI, Inc.
[d] Polyoxyethylene-polyoxypropylene copolymer sold by the BASF-Wyandotte Company.
[e] Hydroxypropyl methylcellulose sold by the Dow Chemical Company.
[f] A Celanese Corporation trademark for 3-(triethylamino)-2-hydroxy-propyl guar chloride.
[g] Methyl cellulose sold by the Dow Chemical Company.

EXAMPLE II

Toothpaste compositions can comprise CMC, water and solid polyethylene glycol. Previously, it took several hours to carefully incorporate a dry powdered CMC gum into a sorbitol blend containing water. Almost always, lumping of improperly wetted CMC powder occured.

The old process involved addition of dry CMC, sodium benzoate and sodium saccharin to a reactor filled with sorbitol and water. A triblender mechanism was employed to accomplish these dry powder additions. Molten polyethylene glycol (1540 molecular weight) hereinafter identified as PEG 1540, was then added into the aqueous sorbitol containing reactor. The resultant blend is known as a Liquid Premix. Once formed, Liquid Premix was conducted to the main toothpaste reactor. Abrasives, actives and other dentifrice components were therein combined.

In the new procedure, a slurry of PEG 1540, water, sodium benzoate and CMC gum was first prepared. The slurry did not gel or lump. This was unexpected. Once prepared, the slurry could be rapidly added to the aqueous sorbitol mixture without adverse effect on physical properties.

The change in process offered the following advantages:
1. Since the gum slurry did not swell, a mixture could be prepared in advance or simultaneous to the charging of the main tank with sorbitol, water and saccharin. Here was the major time savings. Productivity increased by at least 50%.
2. The resultant Liquid Premix was lump-free. Accordingly, extra mixing to break up the large lumps experienced with the old process was no longer required.
3. All the gum was fully utilized to bind up excess water and maintain toothpaste stability. Material was no longer wasted.
4. The troublesome, messy Triblender system could be eliminated. It had to be frequently taken apart and cleaned to attain maximum frequency. The resultant "slippery" premix on the floor was a constant safety hazard.
5. With the new process, toothpaste production was increased without the need for larger or additional manufacturing tanks. Aside from increased cost and time that would be required to install a larger system, space would also be a problem.

TYPICAL FORMULATION LIQUID PREMIX

| Old Process | | |
|---|---|---|
| Ingredient | | Parts |
| Sorbitol (70% solids) | | 61.19 |
| Deionized Water | | 2.93 |
| Sodium Benzoate | | 0.08 |
| Sodium Saccharin | | 0.30 |
| CMC Gum | | 0.40 |
| PEG 1540 | | 5.00 |
| Total | | 69.90 |
| New Process | | |
| Main Reactor: | | |
| Ingredient | | Parts |
| Sorbitol (70% solids) | | 61.19 |
| Deionized Water | | 0.79 |
| Sodium Saccharin | | 0.30 |
| Gum Slurry: | | |
| PEG 1540 | 5.00 | |
| Deionized Water | 2.14 | |
| Sodium Benzoate | 0.08 | |
| CMC Gum | 0.40 | |
| | 7.62 | 7.62 |
| Total | | 69.90 |

Once prepared, Liquid Premix is combined with abrasives and certain other dentifrice components. These ingredients account for the remaining 30% of the toothpaste formulation.

EXAMPLE III

A toothpaste comprised of carrageenan and PEG 1540 can be prepared according to the method of this invention. Both old and new processes are outlined below. With the new process, a lump free dentifrice will be obtained.

TYPICAL FORMULATION LIQUID PREMIX

| Old Process | | |
|---|---|---|
| Main Reactor: | | |
| Ingredient | | |
| Sorbitol (70% solids) | | 14.00 |
| Water, Deionized | | 31.24 |
| Sodium Saccharin | | 0.25 |
| Sodium Benzoate | | 0.08 |
| Carrageenan | | 0.40 |
| PEG 1540 | | 5.00 |
| | | 50.97 |
| New Process | | |
| Main Reactor: | | |
| Ingredient | | |
| Sorbitol (70% solids) | | 14.00 |
| Water, Deionized | | 30.64 |
| Sodium Saccharin | | 0.25 |
| Gum Slurry: | | |
| PEG 1540 | 5.00 | |
| Deionized Water | 0.60 | |
| Sodium Benzoate | 0.08 | |
| Carrageenan | 0.40 | |
| | 6.08 | 6.08 |
| | | 50.97 |

Once prepared, Liquid Premix is combined with abrasives and certain other dentifrice components.

These ingredients account for the remaining 50% of the toothpaste formulation.

EXAMPLE IV

Xanthan gums are also utilized in toothpastes. This example illustrates a formulation with xanthan gum and PEG 1540. When the new process is employed, a lump free dentifrice will be obtained.

| TYPICAL FORMULATION LIQUID PREMIX | | |
| --- | --- | --- |
| Old Process | | |
| Main Reactor: Ingredient | | |
| Sorbitol (70% solids) | | 56.27 |
| Water | | 1.50 |
| Sodium Benzoate | | 0.08 |
| Xanthan Gum | | 0.40 |
| PEG 1540 | | 5.00 |
| | | 63.25 |
| New Process | | |
| Main Reactor: Ingredient | | |
| Sorbitol (70% solids)[a] | | 56.27 |
| Gum Slurry: | | |
| PEG 1540 | 5.00 | |
| Deionized Water | 1.50 | |
| Sodium Benzoate | 0.08 | |
| Xanthan Gum | 0.40 | |
| | 6.98 | 6.98 |
| | | 63.25 |

[a]Contains 29–30% water

Once prepared, Liquid Premix is combined with abrasives and certain other dentrifrice components. These ingredients account for the remaining 36% of the toothpaste formulation.

EXAMPLE V

Brushless shaving creams may be prepared by the method of this invention. Polyethylene glycol, stearic acid, lanolin and terpineol are first melted together at 60° C. Triethanolamine is then added. Aqueous potassium hydroxide is charged to the main reactor.

In accordance with this invention, an additional portion of polyethylene glycol (300 M.W.:1500 M.W., 1:1) is combined with water. Hydroxyethyl cellulose, is added thereto. The aqueous alcohol-gum slurry is charged to the main reactor. When the contents have cooled at about 45° C., propylene glycol, perfume, more water and zinc stearate are added with thorough mixing. A lump-less shaving cream can thereby be produced.

| BRUSHLESS SHAVING CREAM | | |
| --- | --- | --- |
| New Process | | |
| Main Reactor: Ingredient | | |
| Polyethylene Glycol | | 6.75 |
| Stearic Acid | | 11.5 |
| Lanolin | | 4.0 |
| Terpincol | | 0.1 |
| Triethanolamine | | 1.0 |
| Potassium hydroxide | 0.5 | |
| Water | 38.5 | |
| | 39.0 | 39.0 |
| Gum Slurry: | | |
| Polyethylene Glycol | 6.75 | |
| Water | 2.00 | |
| Hydroxyethyl cellulose (low viscosity) | 0.7 | |
| | 9.45 | 9.45 |
| Final Component: | | |
| Water | | 13.0 |
| Propylene Glycol | | 10.0 |
| Perfume | | 0.2 |
| Zinc Stearate | | 5.0 |
| | | 100.0 |

The foregoing description and examples illustrates selected embodiments of the present invention. In light thereof, various modifications will be suggested to one skilled in the art, all of which are within the spirit and purview of this invention.

What is claimed is:

1. A method of formulating a lump-free alcohol-water-gum containing composition comprising:
   (a) preparing a blend of a minor amount of water and a major amount of a polyethylene glycol, solid at room temperature;
   (b) introducing into the polyethylene glycol-water blend a hydrophilic gum resulting in a final weight ratio water:gum of about 20:1 to 1.3:1 and polyethylene glycol:gum ratio of about 25:1 to 2:1;
   (c) intimately mixing the resultant slurry; and
   (d) feeding the slurry into a water containing formulation.

2. A method according to claim 1 wherein the gum is selected from the group consisting of sodium carboxyalkyl cellulose, alkyl cellulose, hydroxyalkyl alkylcellulose and mixtures thereof wherein alkyl is $C_1$–$C_4$.

3. A method according to claim 1 wherein the gum is sodium carboxymethyl cellulose.

4. A method according to claim 1 wherein the gum is hydroxymethyl propylcellulose or methylcellulose.

5. A method according to claim 1 wherein the gum is selected from the group consisting of xanthan, carrageenan, guar, quaternary guar and mixtures thereof.

6. A method according to claim 1 wherein the water to gum ratio is about 6:1 to about 2:1.

7. A method for preparing a personal care product selected from the group consisting of toothpaste, shampoo, shaving cream and cosmetics prepared at least in part by the method of claim 1.

8. A product prepared according to the process of claim 1.

9. A personal care product selected from the group consisting of toothpaste, shampoo, and cosmetics prepared at least in part by the method of claim 1.

* * * * *